United States Patent [19]

Van Vliet

[11] 4,067,338
[45] Jan. 10, 1978

[54] DISPOSABLE DIAPER WITH IMPROVED TAPE FASTENER

[75] Inventor: Raymond August Van Vliet, Castle Rock, Wash.

[73] Assignee: Weyerhaeuser Company, Tacoma, Wash.

[21] Appl. No.: 743,896

[22] Filed: Nov. 22, 1976

[51] Int. Cl.² .................. A61F 13/16; A41B 13/02
[52] U.S. Cl. .................................. 128/287; 128/284; 24/73 VA
[58] Field of Search .............. 128/284, 287, 290 R; 24/67, 73 VA, DIG. 11

[56] References Cited

U.S. PATENT DOCUMENTS

| | | | |
|---|---|---|---|
| 3,616,114 | 10/1971 | Hamaguchi et al. | 128/287 UX |
| 3,867,940 | 2/1975 | Mesek et al. | 128/287 |
| 3,900,031 | 8/1975 | Endres et al. | 128/287 |
| 3,970,086 | 7/1976 | Cheslow | 128/287 |
| 3,999,546 | 12/1976 | Feldman et al. | 128/284 |
| 3,999,547 | 12/1976 | Hernandez | 128/284 |
| 4,020,842 | 5/1977 | Richmond et al. | 128/287 |

Primary Examiner—Aldrich F. Medbery

[57] ABSTRACT

An improved diaper fastener system has particular application to a conventional disposable diaper having a generally rectangular-shaped absorbent pad or filler disposed between a fluid-permeable top cover sheet and a thermoplastic film backing sheet. The fastener system is comprised of a pair of substantially conventional pressure-sensitive fastener tapes but having stress-accepting inserts traversing a certain distance between the release liner and a position on the fixed portion of the fastener tape. When the attachment portion of the tape is opened for use, the applied forces are at least partially accepted by the stress-accepting insert, transferring it through the release liner to the cover sheet which is stronger than the plastic film backing sheet.

8 Claims, 3 Drawing Figures

DISPOSABLE DIAPER WITH IMPROVED TAPE FASTENER

BACKGROUND OF THE INVENTION

This invention relates generally to disposable diapers and more particularly to an improved fastener system for such diapers.

Conventional disposable diapers, in one popular construction, are comprised of a generally rectangular absorbent pad or filler disposed between a fluid-permeable body facing top sheet and a fluid-impermeable plastic film backing sheet. The filler may be comprised of standard commercially available fluff pulp while the top sheet may be comprised of a standard commercially available nonwoven material and the backing sheet may be comprised of a thin sheet of polyethylene. At the lateral side edges of the diaper the backing sheet can be folded around the edges and sealed so that a narrow strip overlies the top sheet while at the ends of the filler the backing sheet and top sheet are bonded together and extend past the top and bottom edges of the filler providing a foldable flap to tuck in against the top sheet upon diapering.

The tape fastener system, in a typical construction, is comprised of a pair of pressure-sensitive tapes that are adhered to the backing sheet at one end of the diaper. Usually the tapes are comprised of two separate parts with one part being the tape having a fixed portion permanently bonded to the backing sheet with the other attachment portion extending, in the closed position, around the side edge to overlie the release liner which is permanently bonded to the top sheet. When ready for use the attachment portion of the tape is removed from the release liner and pulled so as to extend outwardly from the side edge thereby pulling on the plastic backing sheet with the common attachment forces.

A major problem with tapes that are fixed to the plastic backing sheet is that when a person applies tension to the tape, stresses are created within the plastic film that often cause the film to rupture and tear making the diaper unusable. This problem has been recognized and at least two solutions have been proposed. One solution may be seen by referring to U.S. Pat. No. 3,867,940 issued Feb. 25, 1975 to Mesek et al wherein a reinforcing scrim having a higher modulous of elasticity than the plastic film backing sheet is adhered to the thin film in a location at least in the vicinity of where the tape is adhered to the thin film. This construction allows some of the stress to be accepted by the stronger reinforcing material. Another solution may be seen by referring to U.S. Pat. No. 3,900,031 issued Aug. 19, 1975 to Endres et al in which the tape fasteners are attached to the backing sheet in an area where the top sheet is adhered thereto along the entire top edge. In the Endres et al construction the filler material terminates so that it does not extend all the way in the longtudinal direction to the sealed top end margin of the diaper. Each of these tape fastener constructions operates to solve the problem for the particular diaper construction; however, other solutions for various reasons are continually being sought and the present invention is a solution unlike those known in the art.

Accordingly, from the foregoing, one object of the present invention is to provide an improved diaper fastener system that reduces tearing of the plastic film backing sheet.

Another object of the invention is to provide a reinforced structure at the tape attachment area which is economical to manufacture.

Still a further object of the present invention is to reduce tearing of the plastic film backing sheet while still substantially retaining a conventional tape fastener construction.

These and other objects of the invention will become more apparent upon reading the description to follow while referring to the drawings.

SUMMARY OF THE INVENTION

Briefly stated, this invention is comprised in one form of a disposable diaper of the type having a generally rectangular absorbent pad or filler disposed between a fluid-permeable body contacting top sheet and a fluid-impermeable plastic film backing sheet together with a pair of pressure-sensitive fastener tapes with one end of each tape fixed to the backing sheet at a conventional position along the side edges. A conventional release liner is fixed to the top sheet and has extending outwardly therefrom, affixed at an end edge on the lower surface, a stress-accepting insert member which traverses a distance from the edge of the release liner around the diaper side edge where it is fixedly bonded to the fixed portion of the tape. When the attachment portion of the tape is pulled outwardly, a substantial amount of the stress will be accepted by the insert member and transferred through the release liner to the stronger top sheet material.

DESCRIPTION OF THE PREFERRED EMBODIMENT

Figure 1:
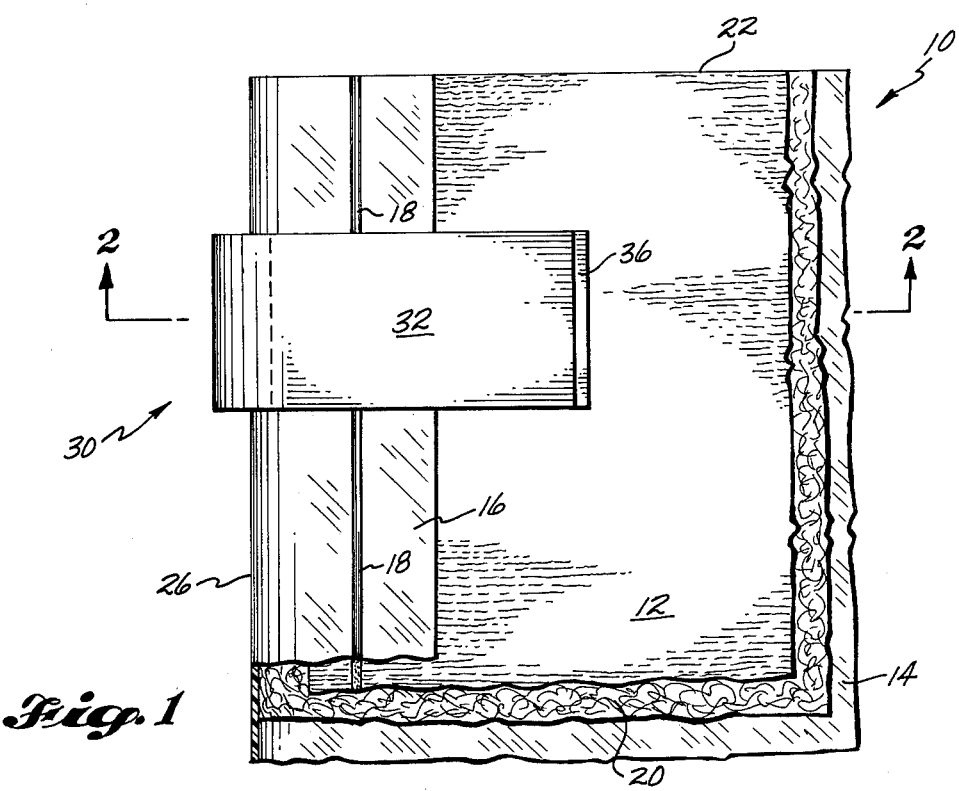
FIG. 1 is a cutaway plan view showing one corner of a conventional disposable diaper having the tape fastener system in its closed position.
Figure 2:
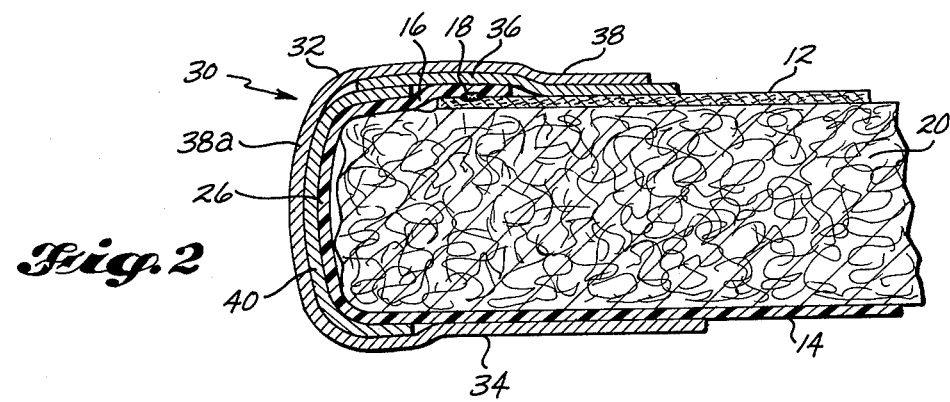
FIG. 2 is a cross-section taken along line 2—2 of FIG. 1 and shows the details of the tape fastener structure.

Referring first to FIG. 1, a brief general description will be given of the conventional disposable diaper suitable for use with the present invention. A portion of a generally rectangular disposable diaper is indicated at 10. The typical disposable diaper 10 is comprised of a liquid-permeable body contacting top sheet 12 which is the size of the rectangular planar area and is normally comprised of, for example, a typical thin nonwoven material having relatively high cross-directional strength. The backing sheet 14 is comprised of a liquid-impermeable thin thermoplastic material such as polyethylene and is generally the same size as top sheet 12 with a standard exception being the top-side marginal portions 16 which are folded around the side edges and bonded to top sheet 12. A narrow bonding line 18 along the length of each marginal portion 16 serves to adhere the plastic material to the top sheet material. The bonding line may be comprised of any suitable adhesive such as a hot melt. The top-side marginal portions 16 provide a gasket-like function when in use. Disposed between the top sheet 12 and backing sheet 14 is the substantially rectangular absorbent pad or filler 20. The filler 20 may be comprised of any suitable liquid absorbing material such as, for example, typical commercially available fluff pulp. Along each top and bottom marginal end 22 the top sheet and backing sheet material is bonded together to enclose filler material 20. Along each marginal side edge 26 a typical construction is as depicted in FIG. 2 where the plastic backing sheet 14 is folded around the side edge of filler 20 and overlies a portion of top sheet 12 being bonded thereto along the longitudinally extending bonding line 18 to form top-side marginal portions 16.

Turning now to a specific description of the tape fastener system which incorporates the present invention, reference will be made to FIGS. 1-3. One of a pair of tape fasteners comprising the tape fastener system is generally indicated at 30. The other fastener of the pair would be positioned laterally opposite the one shown and would be constructed in the same manner. The tape fastener 30 is typical in all respects with one major exception. In the closed position as depicted in FIGS. 1 and 2 the tape 32 has a fixed portion 34 permanently fixing the tape to the plastic backing sheet 14. A typical release liner 36 is permanently attached to at least part of the top sheet 12 and normally to a part of the side marginal portion 16 as well. Release liner 36 is fixedly attached to the substrate along one surface while providing a release surface on the other surface. The attachment portion 38 of tape 32 is folded about the side edge 26 of disposable diaper 10 so as to overlay the release surface of release liner 36. Serving to traverse the distance from the outermost end edge of release liner 36 around the fold of the backing sheet material to a position coplanar with the backing sheet material on the back surface of the diaper is the stress-accepting insert member 40. The insert members 40 are comprised of material stronger than the backing sheet material. Each tape fastener 30 has an insert member 40 and each is substantially the same width as tape 32 and release liner 36 while its longer side edges are substantially colinear with the longer side edges of tape 32 and release liner 36. One end edge of insert number 40 is positioned so as to underlie the bottom surface of release liner 36 and thereby becomes bonded to liner 36 since its bottom surface is an adhesive surface. The inner surface of insert number 40 is in a loose relationship with the plastic backing sheet material. In the closed position of tapes 32, part 38a of the attachment portions 38 will overlie the outer surface of insert members 40 and become bonded thereto in a substantially permanent stress-transferring relationship.

Figure 3:
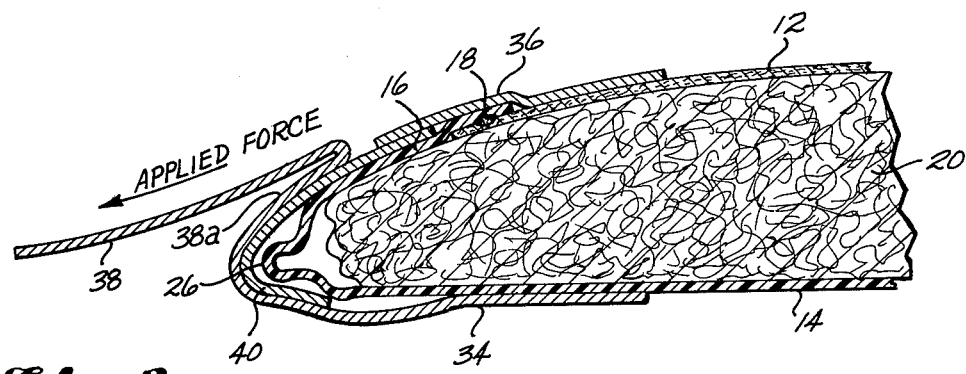
FIG. 3 is a similar cross-section through the tape fastener system but shows the tape fastener structure in a stressed condition.

Turning now to FIG. 3 a description will be given of the tape fastener as it is being used and the function of the present invention should thereby become abundantly clear. The user, that is the person who is applying the diaper, peels back the attachment portion 38 of tape 32 in the typical manner. As the attachment portion is peeled back from release liner 36, it will ultimately reach the outer surface of stress-accepting insert member 40. As the applied force continues to be exerted in the direction indicated on FIG. 3, the insert member 40 and other parts will become deformed as indicated. However, the force will be at least partially transferred from the attachment portion 38 to insert member 40 then through release liner 36 to the top sheet 12 where it will be distributed over substantially stronger material compared to the weaker backing sheet material. Thus the in-use forces are effectively transferred away from the weak plastic material allowing the forces to be accepted by the stronger materials within the diaper structure.

While a perferred embodiment of the present invention has been described, it is to be understood that many changes and modifications may be made without departing from the scope of the invention. All such modifications are intended to be included within the scope of the appended claims.

What is claimed is:

1. In an absorbent article of the type having a fluid-permeable body contacting top sheet, a fluid-impermeable plastic film backing sheet, and an absorbent filler disposed therebetween together with a tape fastener system along at least one edge of the article, the improvement comprising:
   at least one tape having a fixed portion attached to the plastic film backing sheet and an attachment portion having an open and closed position,
   a release liner fixed to at least a portion of the fluid-permeable top sheet in a position whereby the tape attachment portion can overlay at least part of the release liner in its closed position, and
   a stress-accepting insert member attached to and extending outwardly from the edge of the release liner around a side edge of the article to a position where it is attached to at least a portion of the fixed portion of the tape,
   said insert members being arranged and adapted to accept in-use stresses, transferring a substantial portion of them when accepted from the attachment portion of the tape to at least one material within the article that has greater strength than the backing sheet.

2. The improvement as in claim 1 in which one end edge of the insert member underlies the bottom surface of the release liner and extends around the side edge of the article to underlie the fixed portion of the tape.

3. The improvement as in claim 1 in which all of the attachment areas are adhesive bonds.

4. The improvement as in claim 1 in which the inner surface of the insert member is in a loose relationship with the fluid-impermeable backing sheet.

5. The improvement as in claim 1 in which at least a portion of the attachment portion of the tape overlies the insert member and is adhesively bonded thereto.

6. A pressure-sensitive tape fastener, comprising:
   a tape member having one adhesive surface and one adhesive free surface, the adhesive surface on one end thereof providing a means for its attachment to a first protion of an object, and the adhesive surface on the other end providing a means for its attachment to a different portion if the object,
   a release liner member having one surface a portion of which is releasably attached to a portion of the tape member at said one end thereof along its adhesive surface, a second portion of said one surface defining a means for fixedly attachment to said object first portion, and
   a stress-accepting insert member fixedly attached to at least a portion of said second surface of the release liner member and extending for a distance over the adhesive surface of the tape member but terminating short of said the other end thereof.

7. A pressure-sensitive tape fastener as in claim 6 in which all of the members have substantially colinear side edges.

8. A pressure-sensitive tape fastener as in claim 6 in which the surface of the insert member opposite the surface juxtaposed to the tape member is a nonadhesive surface.

* * * * *